(12) United States Patent
Banerjee

(10) Patent No.: US 11,129,964 B2
(45) Date of Patent: Sep. 28, 2021

(54) TRAPPING SHEATHS AND GUIDE CATHETERS

(71) Applicant: The Board of Regents of The University of Texas System, Austin, TX (US)

(72) Inventor: Subhash Banerjee, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 619 days.

(21) Appl. No.: 13/801,263

(22) Filed: Mar. 13, 2013

(65) Prior Publication Data
US 2014/0276611 A1 Sep. 18, 2014

(51) Int. Cl.
*A61M 25/01* (2006.01)
*A61M 25/00* (2006.01)

(52) U.S. Cl.
CPC ...... *A61M 25/0169* (2013.01); *A61M 25/003* (2013.01); *A61M 2025/0079* (2013.01)

(58) Field of Classification Search
CPC .. A61M 2025/0025; A61M 2025/0035; A61M 25/0075; A61M 2025/0079; A61M 25/1006; A61M 2025/1065; A61M 2039/0297; A61M 2039/0673; A61M 2039/0686; A61M 2025/1013; A61M 25/004; A61M 25/1011; A61M 39/0613; A61M 2039/0626; A61M 39/227; A61M 39/228; A61M 2039/027; A61M 2039/0294; A61M 25/0074; A61M 25/0169; A61M 25/003; A61M 25/00; A61M 25/0067; A61M 25/01; A61M 25/0026; A61M 25/0021; A61M 25/0028; A61M 25/0172; A61B 17/3439; A61B 2017/3441
See application file for complete search history.

(56) References Cited

U.S. PATENT DOCUMENTS

| | | | |
|---|---|---|---|
| 2,919,697 A * | 1/1960 | Kim | A61M 25/1002 604/102.02 |
| 4,875,897 A * | 10/1989 | Lee | A61B 1/0053 604/28 |
| 5,217,434 A | 6/1993 | Arney | 426/115 |
| 5,217,454 A * | 6/1993 | Khoury | A61B 18/245 606/14 |
| 5,299,575 A | 4/1994 | Sandridge | 600/435 |
| 5,300,047 A * | 4/1994 | Beurrier | A61B 17/34 137/487.5 |
| 5,318,532 A * | 6/1994 | Frassica | A61M 25/1002 604/913 |
| 5,348,537 A | 9/1994 | Wiesner et al. | 604/99.04 |
| 5,350,362 A | 9/1994 | Stouder, Jr. | 604/167.03 |

(Continued)

FOREIGN PATENT DOCUMENTS

WO WO2009140546 11/2009

*Primary Examiner* — Jason E Flick
(74) *Attorney, Agent, or Firm* — Norton Rose Fulbright US LLP

(57) ABSTRACT

Introducer sheaths and (e.g., guide) catheters with inflatable trapping elements for trapping and/or stabilizing devices (e.g., guidewires, catheters, and/or the like) in a primary lumen of the sheath or catheter. Such sheaths and catheters may be configured for endovascular, endoscopic, laparoscopic, and/or urological procedures.

18 Claims, 12 Drawing Sheets

(56) References Cited

U.S. PATENT DOCUMENTS

| | | | | |
|---|---|---|---|---|
| 5,441,485 A * | 8/1995 | Peters | A61M 25/1002 | 604/101.01 |
| 5,634,911 A * | 6/1997 | Hermann | A61B 17/3417 | 604/246 |
| 5,792,118 A * | 8/1998 | Kurth | A61M 25/0017 | 604/246 |
| 6,022,342 A | 2/2000 | Mukherjee | A61M 25/01 | 604/523 |
| 6,042,573 A * | 3/2000 | Lucey | A61B 17/3423 | 604/23 |
| 6,171,299 B1 * | 1/2001 | Bonutti | A61B 17/0218 | 128/898 |
| 6,251,084 B1 | 6/2001 | Coelho | | 600/585 |
| 6,270,489 B1 * | 8/2001 | Wise | A61M 25/003 | 604/508 |
| 6,443,912 B1 | 9/2002 | Mazzola et al. | | 600/585 |
| 6,447,489 B1 * | 9/2002 | Peterson | A61B 17/3439 | 600/204 |
| 6,692,459 B2 * | 2/2004 | Teitelbaum | A61M 39/0208 | 604/288.01 |
| 7,094,218 B2 | 8/2006 | Rome et al. | | 604/99.04 |
| 7,563,250 B2 * | 7/2009 | Wenchell | A61B 17/3417 | 604/167.01 |
| 8,221,388 B2 | 7/2012 | Swisher | | 604/530 |
| 8,486,100 B2 * | 7/2013 | Oishi | A61B 17/3403 | 600/115 |
| 8,584,678 B2 * | 11/2013 | Pol | A61B 1/00045 | 128/200.24 |
| 8,617,045 B2 * | 12/2013 | Salama | A61F 2/0009 | 600/29 |
| 8,690,834 B2 * | 4/2014 | Koehler | A61M 39/0613 | 604/167.01 |
| 8,926,508 B2 * | 1/2015 | Hotter | A61B 17/3421 | 600/207 |
| 9,149,173 B2 * | 10/2015 | Scopton | A61B 1/00098 | |
| 2004/0167559 A1 * | 8/2004 | Taylor | A61B 17/3423 | 606/185 |
| 2005/0059934 A1 * | 3/2005 | Wenchell | A61B 17/3439 | 604/167.01 |
| 2005/0131344 A1 | 6/2005 | Godaire | | 604/99.04 |
| 2006/0241671 A1 * | 10/2006 | Greenhalgh | A61B 17/3423 | 606/191 |
| 2007/0088380 A1 | 4/2007 | Hirszowicz | | 606/194 |
| 2008/0109028 A1 * | 5/2008 | Styrc | A61M 39/0613 | 606/194 |
| 2009/0171278 A1 | 7/2009 | Hirszowicz | | 606/194 |
| 2009/0247945 A1 | 10/2009 | Levit | | 604/313 |
| 2009/0287147 A1 | 11/2009 | Wenchell | | 604/164.03 |
| 2009/0326468 A1 * | 12/2009 | Blier | A61B 17/3498 | 604/167.01 |
| 2010/0298775 A1 * | 11/2010 | Berry | A61B 17/3421 | 604/167.03 |
| 2011/0112567 A1 | 5/2011 | Lenker | | 606/194 |
| 2011/0152788 A1 * | 6/2011 | Hotter | A61B 17/3498 | 604/256 |
| 2011/0186053 A1 * | 8/2011 | Pol | A61B 1/00045 | 128/207.15 |
| 2011/0208129 A1 | 8/2011 | Bonnette | | 604/247 |
| 2011/0282301 A1 | 11/2011 | Nielsen | | 604/247 |
| 2012/0271116 A1 | 10/2012 | Koehler | | 604/539 |

* cited by examiner

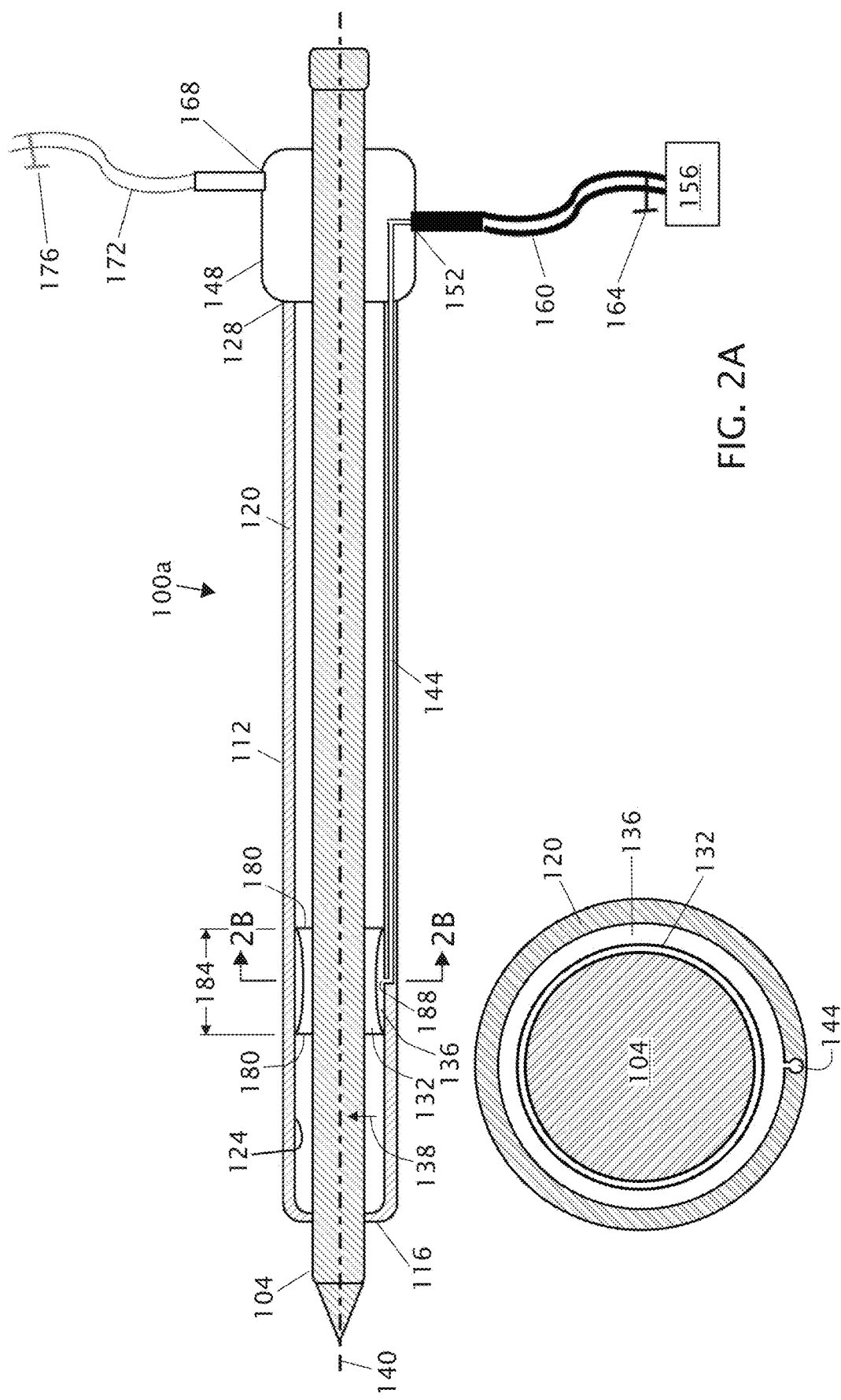

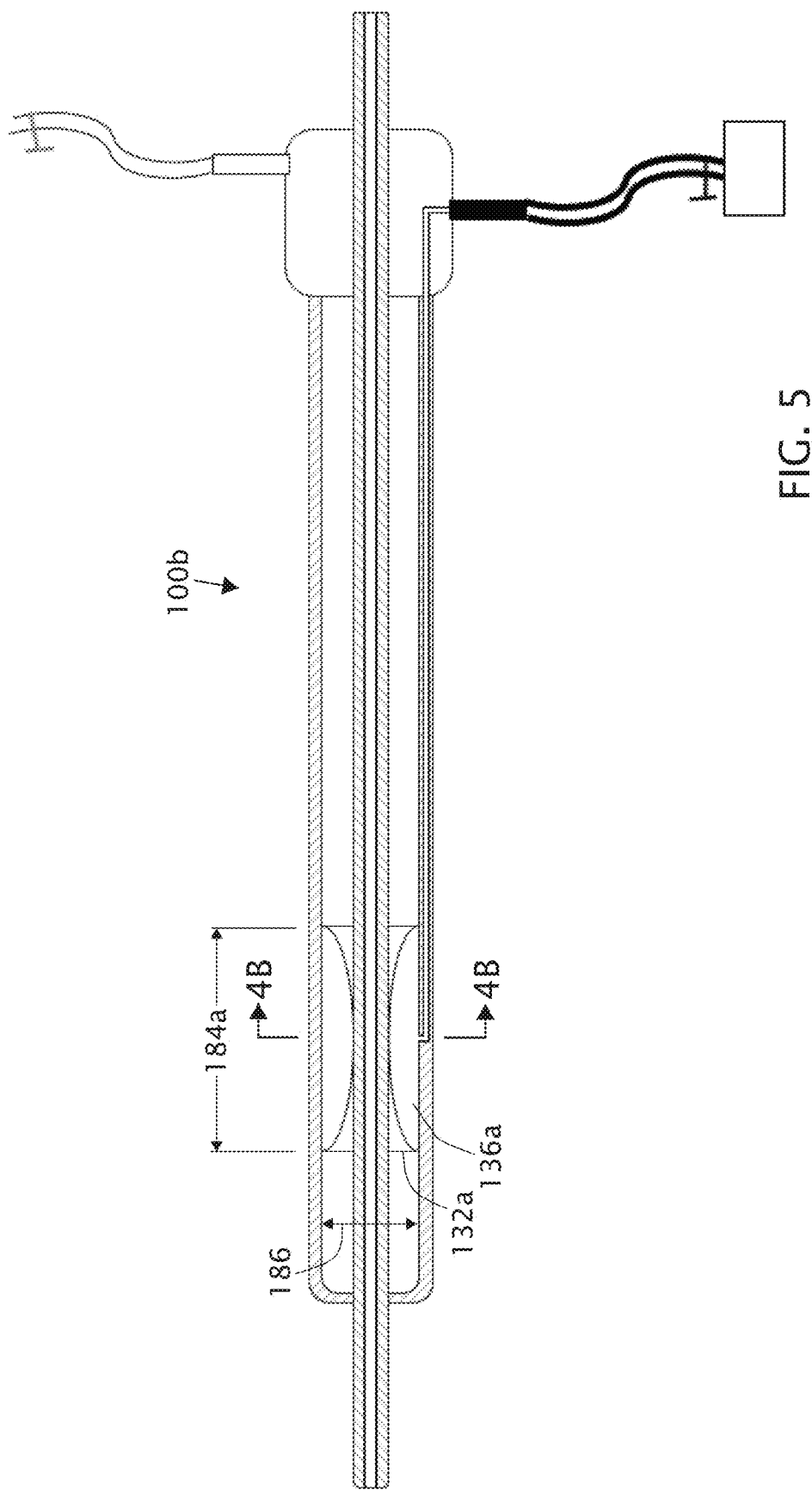

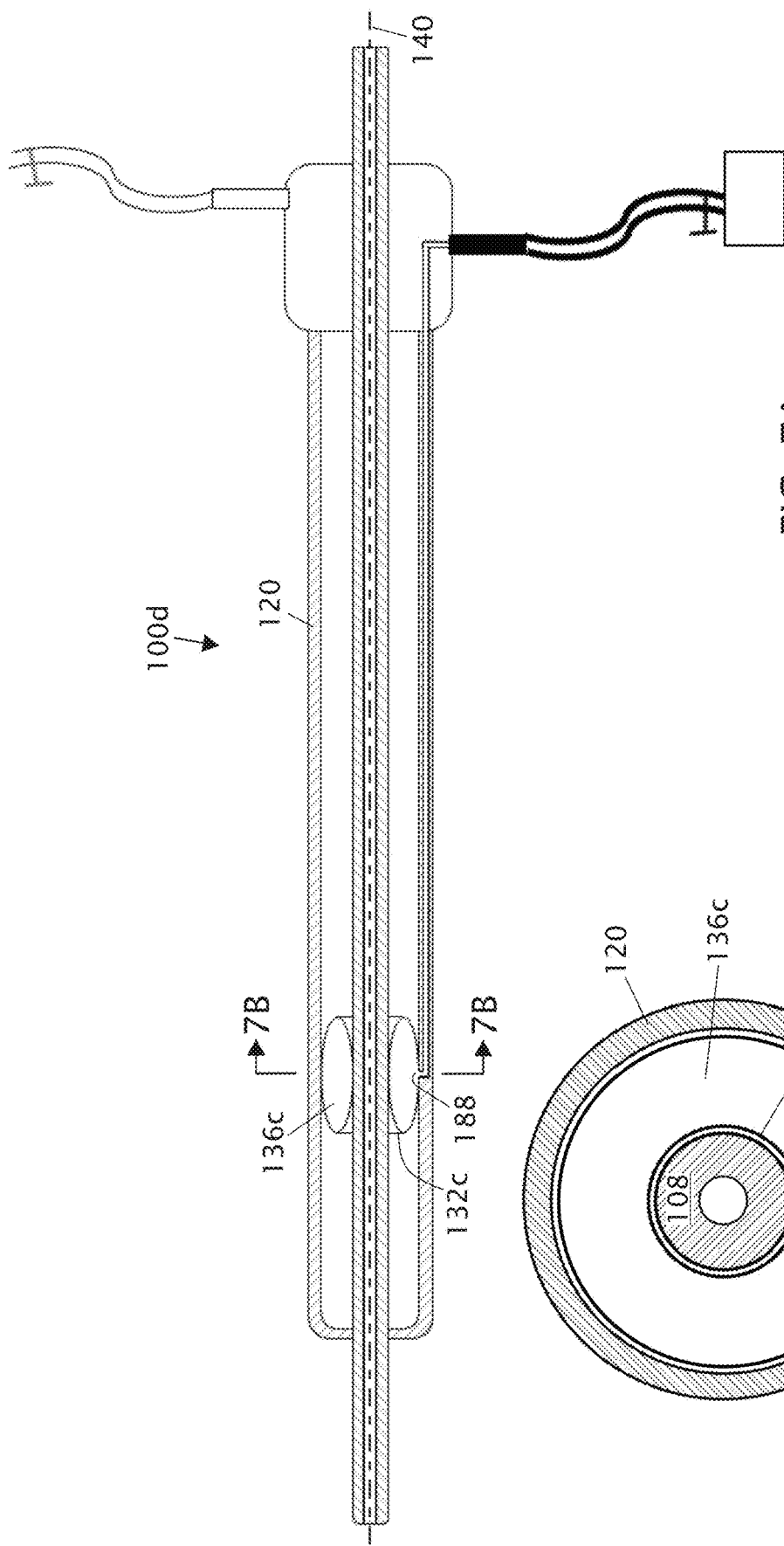

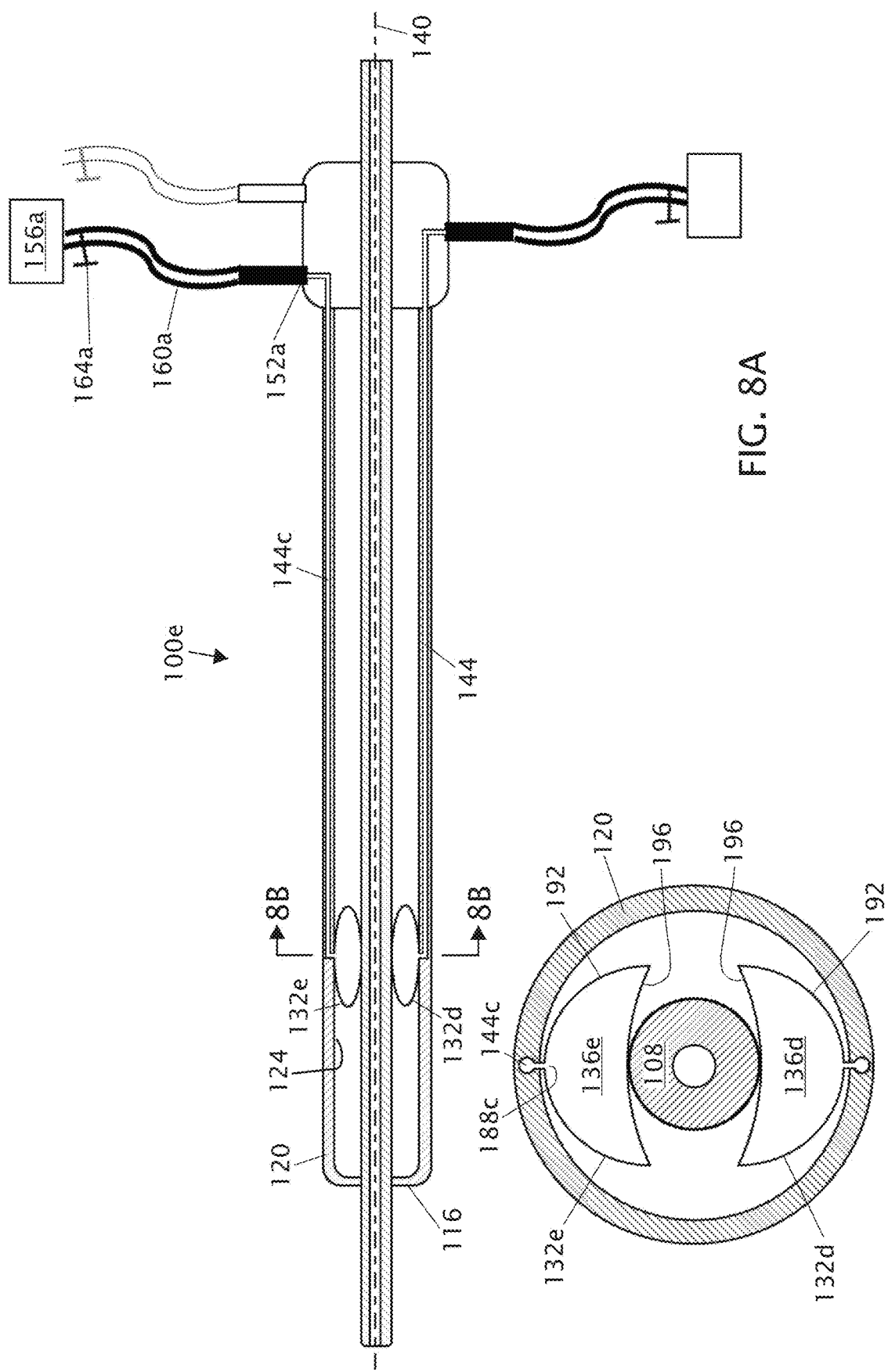

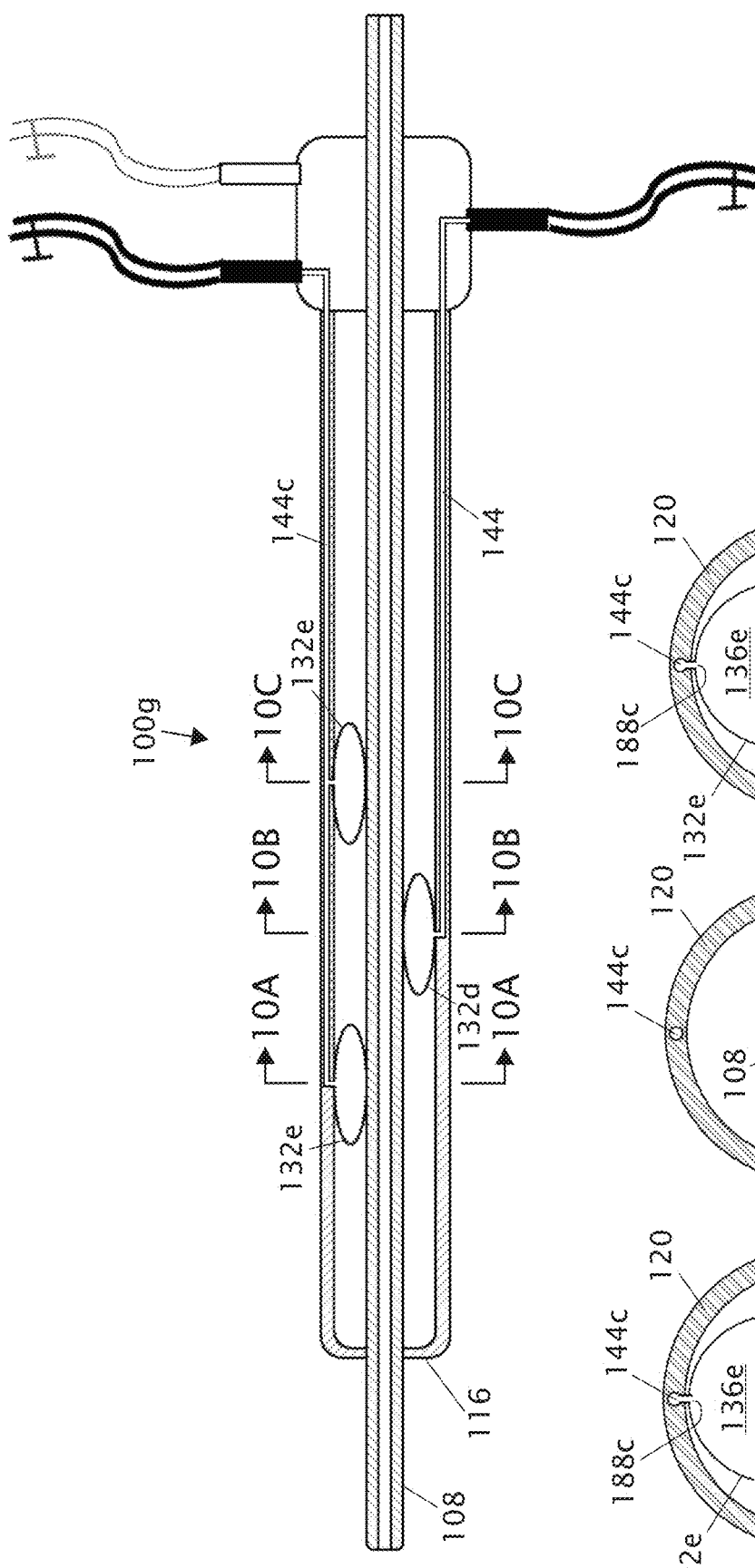
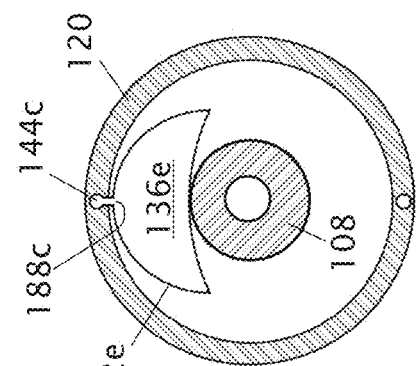
FIG. 10B
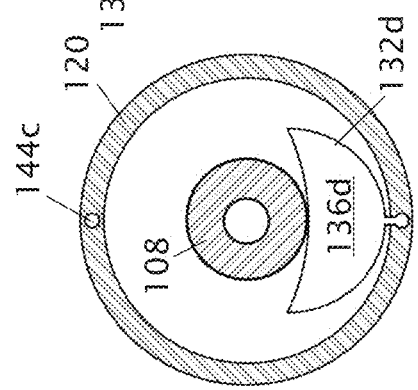
FIG. 10C
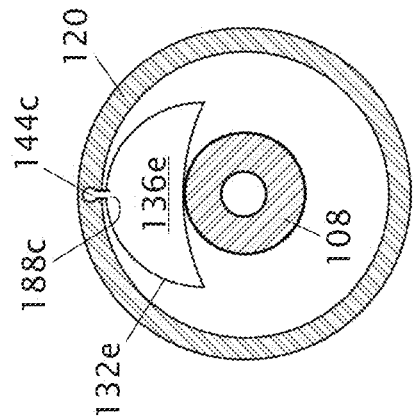
FIG. 10D

TRAPPING SHEATHS AND GUIDE CATHETERS

BACKGROUND

1. Field of the Invention

The invention relates generally to endovascular and surgical interventions and, more particularly, but not by way of limitation, to introducer sheaths and catheters (e.g., guide catheters) with internal, inflatable trapping elements for use during surgical interventions (e.g., endovascular, endoscopic, and/or laparoscopic interventions), and methods utilizing such sheaths and catheters.

2. Description of Related Art

Guide catheters and/or sheaths are generally used in all endovascular procedures. It is estimated that over 8 million such endovascular procedures are performed annually in the United States, and are expected to rise as much as 130% over the next 5 years. Various types of endovascular devices (e.g., catheter, balloon stent, and/or the like) may be used in such procedures, including, for example, over-the-wire devices and short-wire (monorail or rapid exchange) devices. In some procedures, it may be desired to exchange devices (e.g., switch from a short-wire or monorail device to an over-the-wire device, or vice versa, without removing a guide wire) and/or to exchange guide wires without removing a device. Switching from a short-wire or monorail device to an over-the-wire (long shaft) device requires careful backing out of the monorail device and advancement of the long shaft with constant attention and observation of the position of the distal end of the guide wire in the vessel (arterial, venous or lymphatic), generally under X-ray, fluoroscopic, or cineangiographic visualization. These types of visualizations during the exchange of such devices exposes the patient and operator to radiation as careful backing out of the devices is performed with constant attention and observation. Such device exchanges or switches may expose the patient to a risk of distal wire movement, especially forward advancement that can potentially result in vessel perforation or loss of a desired position of the distal end (distal position) of the guide wire in the vessel. These complications may be associated with procedural failure, procedural complications such as dissection, and, in some cases, patient morbidity, increased hospital stay and health care costs, and even mortality. In some instances, a balloon may be deployed (e.g., at or near a distal end of the guide wire) to trap the guide wire in position or resist movement of the guide wire as the devices are backed out and inserted over the guide wire.

SUMMARY

This disclosure includes embodiments of apparatuses and methods.

Embodiments of the present introducer sheaths and (e.g., guide) catheters can include one or more inflatable cuffs or balloon-like structures ("trappers") coupled to the interior of a lumen of the sheath or catheter body to trap and/or stabilize guide wires and other devices within the lumen. Embodiments of the present sheaths and (e.g., guide) catheters can be used in the performance of various procedures, such as, for example, diagnostic angiography of vascular territories, delivery of endovascular devices during endovascular interventions, and retrieval of endovascular devices during or after endovascular interventions (e.g., without the use of additional trapping balloons and/or without the need for X-ray, fluoroscopic, or angiographic guidance). The trappers of the present embodiments can be filled through a secondary lumen of the sheath or catheter, such as, for example, with saline or with a mixture of saline and a contrast agent to facilitate imaging of the trappers. The inclusion of trappers within the present embodiments can limit the exposure of patients and healthcare providers to radiation during procedures, limit the need for additional trapping balloons, and improve device support and stability (which can improve procedural success and safety, potentially reducing costs).

Some embodiments of the present apparatuses comprise: an elongated sheath or (e.g., guide) catheter body having a distal end (e.g., configured for percutaneous insertion into a vessel of a patient), the body having a sidewall defining a primary lumen through which an elongated endovascular device can be inserted into the patient's vessel; an expandable member coupled to the sidewall such that a chamber is configured to be inflated to expand the expandable member in a direction away from the sidewall into the primary lumen; and a secondary lumen in fluid communication with the chamber and configured to deliver fluid to expand the expandable member. In some embodiments, the chamber is annular and extends around the entire primary lumen. In some embodiments, the sidewall and the expandable member cooperate to define the chamber. In some embodiments, the sidewall is inelastic. In some embodiments, the sidewall defines a primary lumen cross-section that is substantially rigid. In some embodiments, the expandable member defines the chamber without the sidewall. In some embodiments, the expandable member has a width measured parallel to a longitudinal axis of the body, the width being more than two times the diameter of the primary lumen.

In some embodiments of the present apparatuses, the expandable member is a first expandable member, the chamber is a first chamber, and the apparatus further comprises: a second expandable member coupled to the sidewall such that a second chamber is configured to be inflated to expand the second expandable member in a direction away from the sidewall into the primary lumen. In some embodiments, the second expandable member is spaced apart from the first expandable member along a longitudinal axis of the body. In some embodiments, the secondary lumen is a first secondary lumen, and the apparatus further comprises: a second secondary lumen in fluid communication with the second chamber and configured to deliver fluid to expand the second expandable member.

In some embodiments of the present apparatuses, the chamber does not extend entirely around a central longitudinal axis of the primary lumen. In some embodiments, the chamber is configured to have a substantially circular cross-sectional shape. In some embodiments, the chamber is configured to have a non-circular cross-sectional shape. In some embodiments, the expandable member has a base portion and a distal portion that is closer to the central longitudinal axis than the base portion, and the base portion has a length that is larger than a length of the distal portion. In some embodiments, the base portion is creased relative to the distal portion. In some embodiments, the expandable member is a first expandable member, the chamber is a first chamber, and the apparatus further comprises: a second expandable member coupled to the sidewall such that a second chamber is configured to be inflated to expand the second expandable member in a direction away from the sidewall into the primary lumen. In some embodiments, the first expandable member and the second expandable member are disposed at substantially equal distances from the distal end. In some embodiments, the first expandable member is disposed directly across the primary lumen from the second expandable member. In some embodiments, the first expandable member is closer to the distal end than the second expandable member. In some embodiments, the secondary lumen is a first secondary lumen, and the apparatus further comprises: a second secondary lumen in fluid communication with the second chamber and configured to deliver fluid to expand the second expandable member.

Some embodiments of the present apparatuses further comprise: a third expandable member coupled to the sidewall such that a third chamber is configured to be inflated to expand the third expandable member in a direction away from the sidewall into the primary lumen. In some embodiments, the first secondary lumen is in fluid communication with the third chamber and configured to deliver fluid to expand the third expandable member. In some embodiments, the first expandable member is closer to the distal end than the second expandable member, and the second expandable member is closer to the distal end than the third expandable member. In some embodiments, the third expandable member is radially aligned with the first expandable member. Some embodiments of the present apparatuses further comprise: a fourth expandable member coupled to the sidewall such that a fourth chamber is configured to be inflated to expand the fourth expandable member in a direction away from the sidewall into the primary lumen; where the first expandable member is radially aligned with the third expandable member, the second expandable member is radially aligned with the fourth expandable member, and the first expandable member is disposed opposite the primary lumen from the third expandable member. In some embodiments, the expandable member comprises polyurethane.

Some embodiments of the present apparatuses further comprise: a fluid source comprising a reservoir configured to be coupled to the one or more secondary lumens. Some embodiments further comprise: a fluid disposed in the reservoir, the fluid comprising saline. In some embodiments, the fluid further comprises a contrast agent.

Some embodiments of the present methods comprise: inserting the distal end of the body of one of the present apparatuses through skin of a patient (e.g., into a vessel of the patient); disposing an elongated surgical device in the primary lumen of the apparatus; and delivering fluid to the chamber to expand the expandable member and stabilize the elongated surgical device. In some embodiments, the elongated surgical device stabilized by the expandable member is a guidewire, and the method further comprises: removing a second elongated medical device from the guidewire while the guidewire is stabilized by the expandable member. Some embodiments further comprise: applying an axial force to force the surgical device through a blockage in the vessel.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 2A-2B, 3A-3B, and 4A-4B, depict cross-sectional views of a first embodiment of the present introducer sheaths and catheters.

FIG. 5 depicts a side cross-sectional view of a second embodiment of the present introducer sheaths and catheters.

FIGS. 7A and 7B depict cross-sectional views of a fourth embodiment of the present introducer sheaths and catheters.

FIGS. 8A and 8B depict cross-sectional views of a fifth embodiment of the present introducer sheaths and catheters.

FIGS. 10A-10D depict cross-sectional views of a seventh embodiment of the present introducer sheaths and catheters.

DESCRIPTION OF ILLUSTRATIVE EMBODIMENTS

Figure 1A:
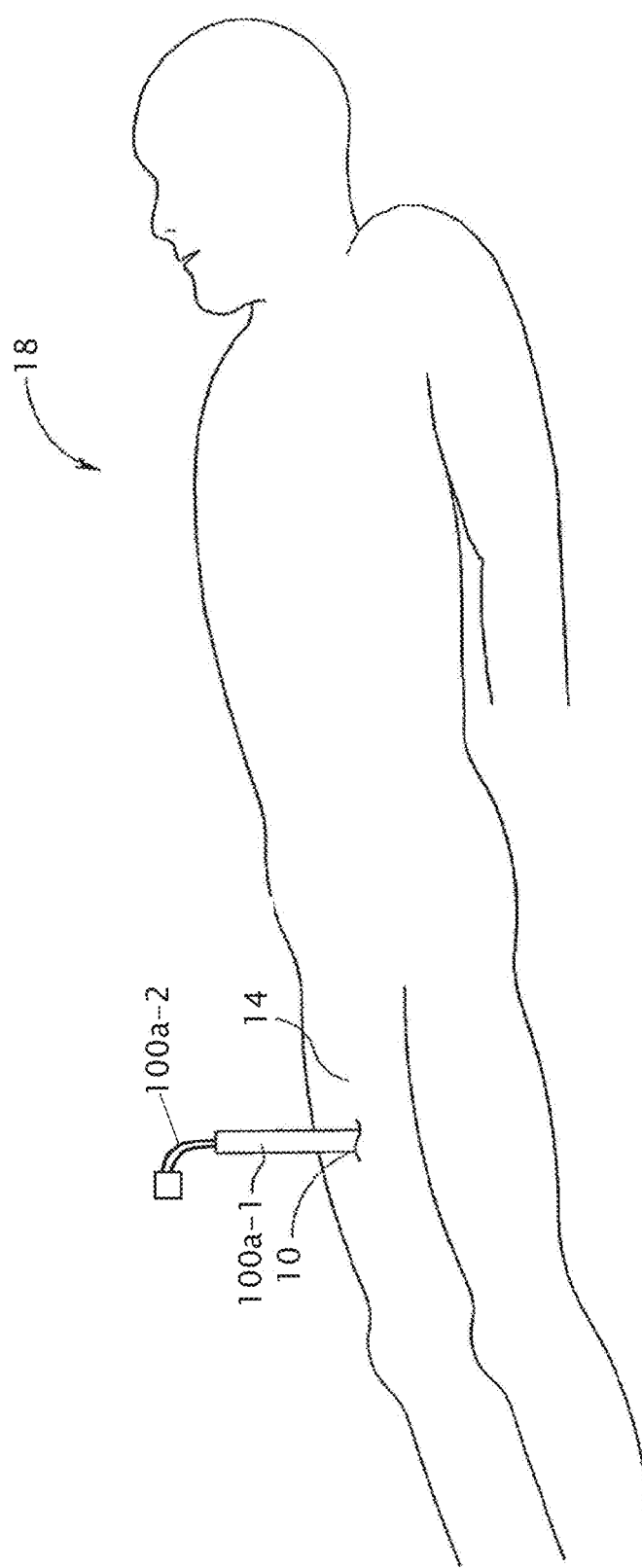
FIGS. 1A and 1B depict perspective and side cutaway views, respectively, of an introducer sheath and a (e.g., guide) catheter extending through a patient's skin and into one of the patient's blood vessels.
Figure 1B:
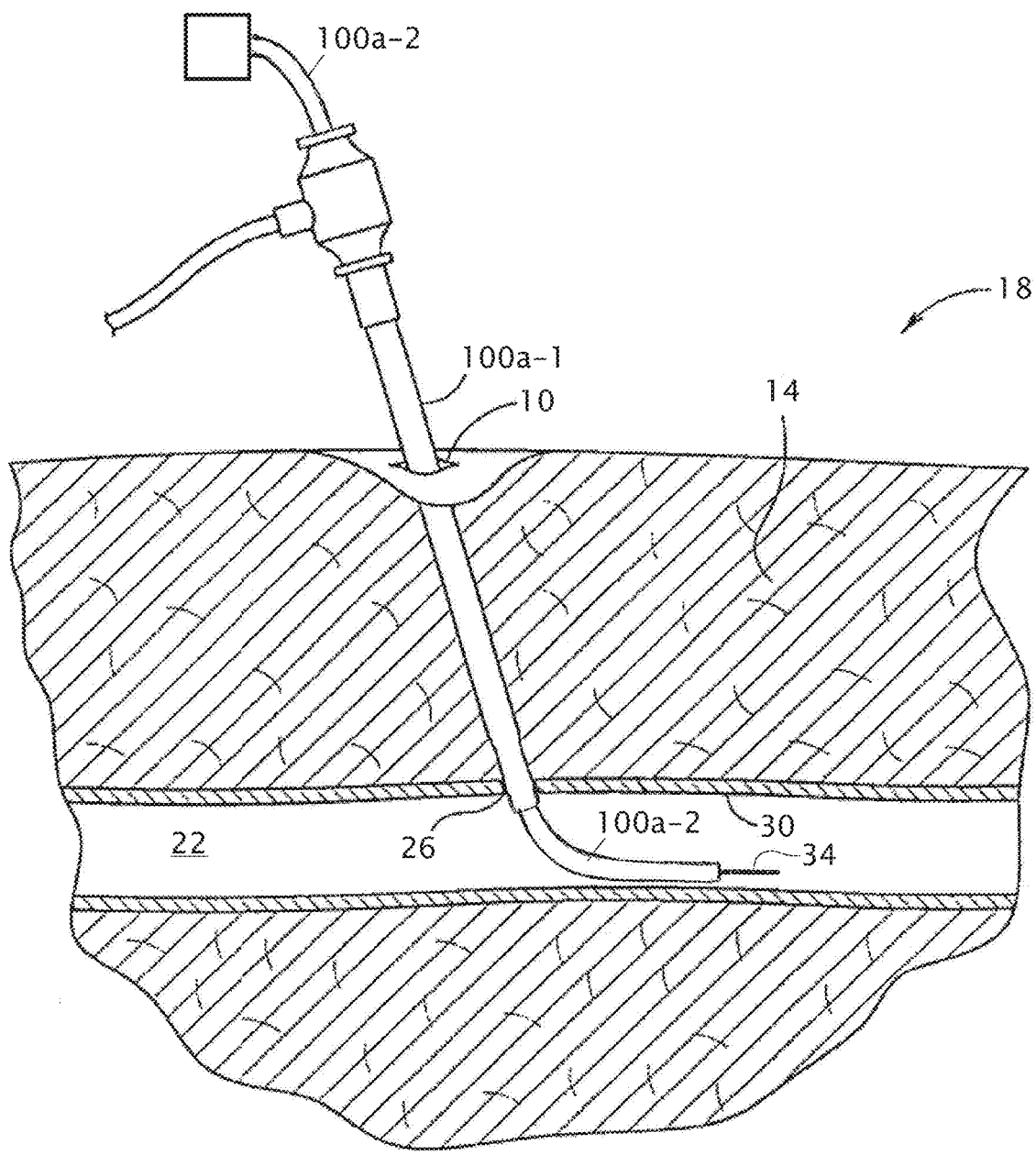

Referring now to the drawings, and more particularly to FIGS. 1A-1B, shown there are perspective and side cutaway views, respectively, of an introducer sheath 100a-1 and a guide catheter 100a-2 extending through a patient's skin and into one of the patient's blood vessels. During the depicted example of a catheterization procedure, a healthcare provider (typically a physician) makes an initial incision 10 in the upper thigh 14 of a patient 18. The provider can then insert a needle (not shown) through the skin via incision 10 to locate the desired blood vessel. In other embodiments, the initial incision is not separately made and a needle is instead inserted through unbroken skin such that the needle generates its own incision through the skin. When a sufficient amount of blood (e.g., bright red, spurting arterial blood) appears through needle, the provider will know the needle has pierced the vessel (e.g., femoral artery 22, as shown) through a vessel incision 26 in wall 30 of the vessel. The provider can then insert a guidewire 34 through the needle and into artery 22, remove the needle, and insert an introducer sheath 100a-1. In the embodiment shown, and as is generally known for introducer sheaths, sheath 100a-1 includes a primary lumen and a valve 38 on its proximal end. Valve 38 can be used to prevent extraneous bleed back and/or to introduce medication into the patient's body through artery 22. Various instruments may be inserted into artery 22 via sheath 100a-1 to perform various medical procedures. For example, a catheter 100a-2 may be inserted through sheath 100a-1 and directed along an arterial path to a target area, such as the heart, to position guidewire 34 to facilitate performance of one or more percutaneous-approach procedures, such as an angioplasty or an angiogram. Additional examples of procedures with which the present embodiments may be used include cardiac catheterization, percutaneous coronary intervention, peripheral arterial endovascular interventions, intracerebral endovascular interventions, renal arterial interventions, aortic endograft placements, and endovenous interventions.

FIGS. 2A-4B depict cross-sectional views of a first embodiment 100a of the present introducer sheath and catheter apparatuses. While the depicted embodiment is generally referred to as an apparatus and designated with the numeral 100a, it should be understood that depicted apparatus 100a is representative of both an introducer sheath and a catheter. For example, present introducer sheaths and catheters each have a generally elongated configuration with a primary lumen. The present introducer sheaths differ from the present catheters in that the introducer sheaths generally have a larger outer diameter and correspondingly larger-diameter primary lumen than the catheters, and the introducer sheaths generally have a shorter length than the catheters, as illustrated, for example, by sheath 100a-1 and catheter 100a-2 in FIGS. 1A and 1B. For example, embodiments of the present guide catheters, which may be referred to as "trapping" guide catheters, can have an outer diameter equal to any one of, or between any two of: 6 French (Fr) (2 mm, 0.079 in.), 7 Fr (2.3 mm, 0.092 in.), 8 Fr (2.7 mm, 0.105 in.), 9 Fr (3 mm, 0.118 in.), and/or 10 Fr 3.3 mm, 0.131 in.). Other embodiments of the present guide catheters may be larger. By way of further example, the embodiments of the present introducer sheaths, which may be referred to as "trapping" sheaths, can have an outer diameter equal to any one of, or between any two of: 6 French (Fr) (2 mm, 0.079 in.), 7 Fr (2.3 mm, 0.092 in.), 8 Fr (2.7 mm, 0.105 in.), 9 Fr (3 mm, 0.118 in.), 10 Fr 3.3 mm, 0.131 in.), 11 Fr (3.7 mm, 0.144 in.), 12 Fr (4 mm, 0.158 in.), 13 Fr (4.3 mm, 0.170 in.), 14 Fr (4.7 mm, 0.184 in.), 15 Fr (5 mm, 0.197 in.), 16 Fr (5.3 mm, 0.210 in.), 17 Fr (5.7 mm, 0.223 in.), 18 Fr (6 mm, 0.236 in.), 19 Fr (6.3 mm, 0.249 in.), 20 Fr (6.7 mm, 0.263 in.), 22 Fr (7.3 mm, 0.288 in.), 24 Fr (8 mm, 0.315 in.), 26 Fr (8.7 mm, 0.341 in.), and/or 28 Fr (9.3 mm, 0.367 in.). Other embodiments of the present introducer sheaths may be larger. For example, some embodiments of the present introducer sheaths are configured for endoscopic, laparoscopic, and/or urological procedures in which larger diameters may be tolerated and/or advantageous. In such embodiments, the present trapping sheaths may be configured and/or used to trap and/or stabilize a variety of surgical tools.

Apparatus 100a is shown in FIGS. 2A-4B in three different configurations. In FIGS. 2A-2B, apparatus 100a is shown with a penetrator 104 configured to facilitate an initial percutaneous insertion of apparatus 100a into a patient's vessel (e.g., artery 22); in FIGS. 3A-3B, apparatus 100a is shown trapping a guide wire 34; and in FIGS. 4A-4B, apparatus 100a is shown trapping a catheter 108 (which could also be a trapping catheter 100a-2, as shown in FIGS. 1A-1B). In the embodiment shown, apparatus 100a comprises: an elongated (sheath or catheter) body 112 having a distal end 116 (e.g., configured for percutaneous insertion into a vessel (e.g., 26) of a patient).

In this embodiment, body 112 has a sidewall 120 defining a primary lumen 124 extending from distal end 116 to a proximal end 128, and through which (primary lumen 124) an elongated endovascular device (e.g., penetrator 104, guide wire 34, and/or catheter 108) can be inserted into the patient's vessel. In the embodiment shown, apparatus 100a also includes an expandable member 132 coupled to sidewall 120 such that a chamber 136 is configured to be inflated to expand expandable member 132 in a direction 138 away from sidewall 120 into primary lumen 124 (e.g., toward and/or beyond a central longitudinal axis 140 of lumen 120), such as is illustrated by the differences in expandable member 132 between FIGS. 2A-2B, FIGS. 3A-3B, and FIGS. 4A-4B. Expandable member 132 can comprise, for example, flexible and/or elastic polyurethane, plastic, and/or other biocompatible material permitting the expandable member to function as described in this disclosure. Importantly, expandable member 132 need not be elastic; the expansion of expandable member may simply be the result of a portion of expandable member being expanded outward relative to sidewall 120 by inflation of chamber 136. In some embodiments, apparatus 100a also includes a secondary lumen 144 in fluid communication with chamber 136 and configured to deliver fluid to expand the expandable member (132). In the embodiment shown, secondary lumen 144 extends through sidewall 120 from proximal end 128 to chamber 136 to permit inflation and deflation of chamber 136 and the resulting expansion and contraction of expandable member 132.

In the embodiment shown, apparatus 100a further comprises a base 148 having a port 152 that is in fluid communication with secondary lumen 144 and that is configured to be coupled to a fluid source (e.g., having a reservoir 156) via a conduit 160 and valve 164. As is known generally for sheaths and guide catheters, base 148 can include a hemostatic valve. In some embodiments, the fluid source includes a syringe. The chamber (136) can be inflated with a fluid such as saline and/or a mixture of saline and contrast agent (e.g., where it is desirable to locate chamber 136 during X-ray guided imaging). In the embodiment shown, base 148 further includes a primary port 168 in fluid communication with primary lumen 124, and configured to be coupled to a fluid source (e.g., a syringe) via a conduit 172 having a valve 176, through which material (e.g., fluids) can be injected into or removed from the patient's vessel (e.g., artery 26). In some embodiments, such as when apparatus 100a is implemented as a catheter, primary port 168 may be omitted.

In the embodiment of FIGS. 2A-4B, chamber 136 is annular and extends around the entire (perimeter of) primary lumen 124, as shown. As a result, as chamber 136 is inflated, expandable member 132 approaches axis 140 substantially evenly from all sides, and urges a trapped device (e.g., catheter 108) toward the center of primary lumen 124, such that expandable member 132 can be considered to be a self-centering expandable member. In the embodiment shown, sidewall 120 and expandable member 132 cooperate to define chamber. More particularly, expandable member 132 is coupled (e.g., by adhesive, plastic welds, and/or the like) to sidewall 120 at seams 180 that define a width 184 and extend around the entire circumference of primary lumen 124 (which has a circular cross-sectional shape, in the embodiment shown) on opposite sides of an opening 188 through which secondary lumen 144 communicates with chamber 136. In some embodiments, secondary lumen 144 can be defined within sidewall 120. In some embodiments, sidewall 120 is substantially inelastic such that, even if body 112 is pressurized or bent, the diameter of primary lumen 124 does not increase (at least without a corresponding decrease in perpendicular diameter, such as if the cross-sectional shape ovals during bending). In some embodiments, sidewall 120 is configured to define a primary lumen cross-section that is substantially rigid (a circular cross-sectional shape) and therefore substantially retains its circular shape at any given point, even if body 112 bends.

Figures 3A, 3B:
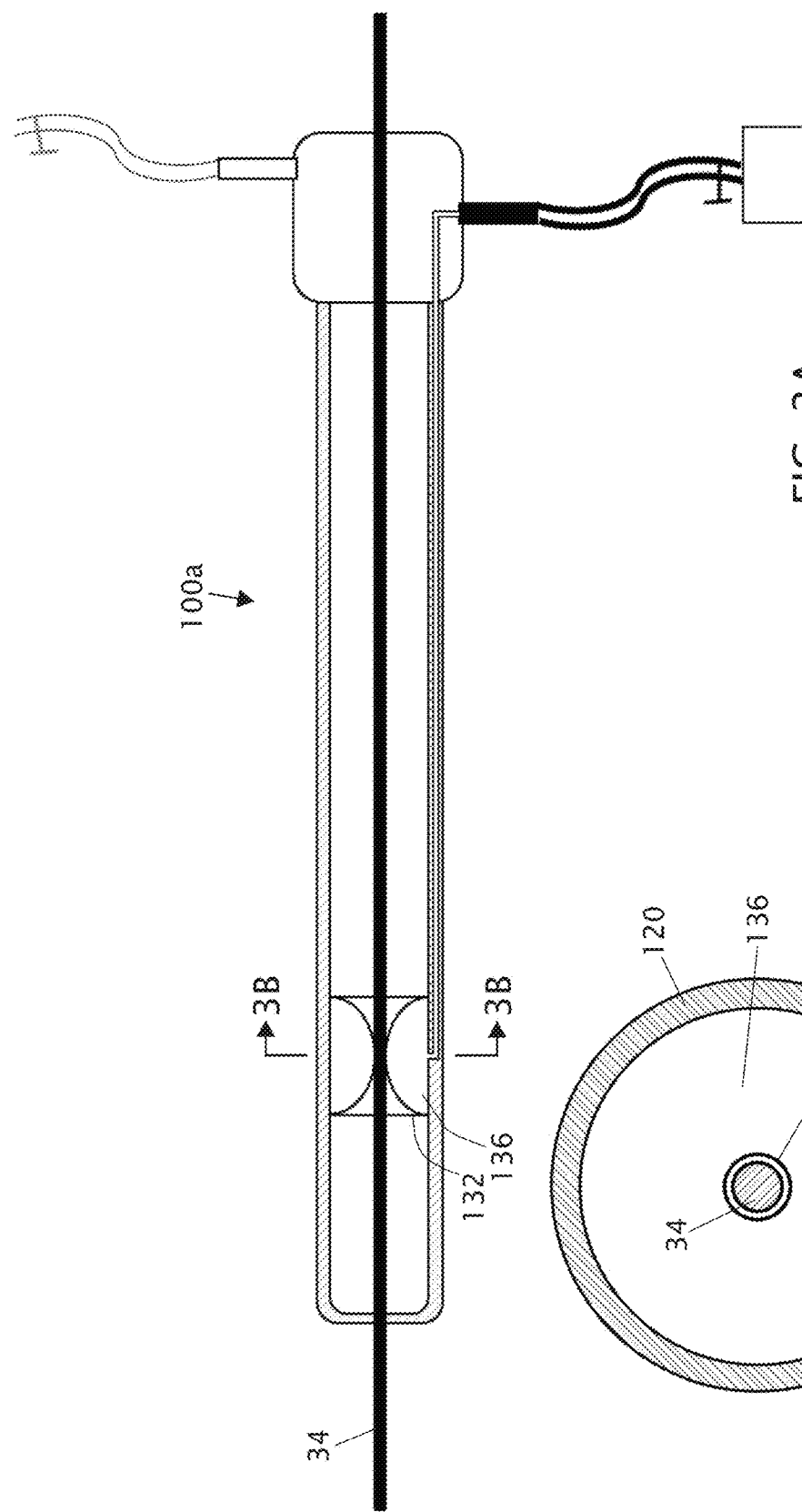

FIGS. 3A-3B depict chamber 136 inflated to expand expandable member 132 to trap a guidewire 34, such as, for example, at an intermediate phase of an endovascular intervention during which expandable member 132 is trapping or stabilizing the guidewire. For example, when apparatus 100a is implemented as a guide catheter (e.g., 100a-2), expandable member 132 can trap or stabilize a portion of the guidewire that is near the distal end of the guidewire (e.g., during removal of a balloon catheter or other over-the-wire device or as other devices are exchanged) to reduce movement of the distal end of the guidewire.

Figure 4A:
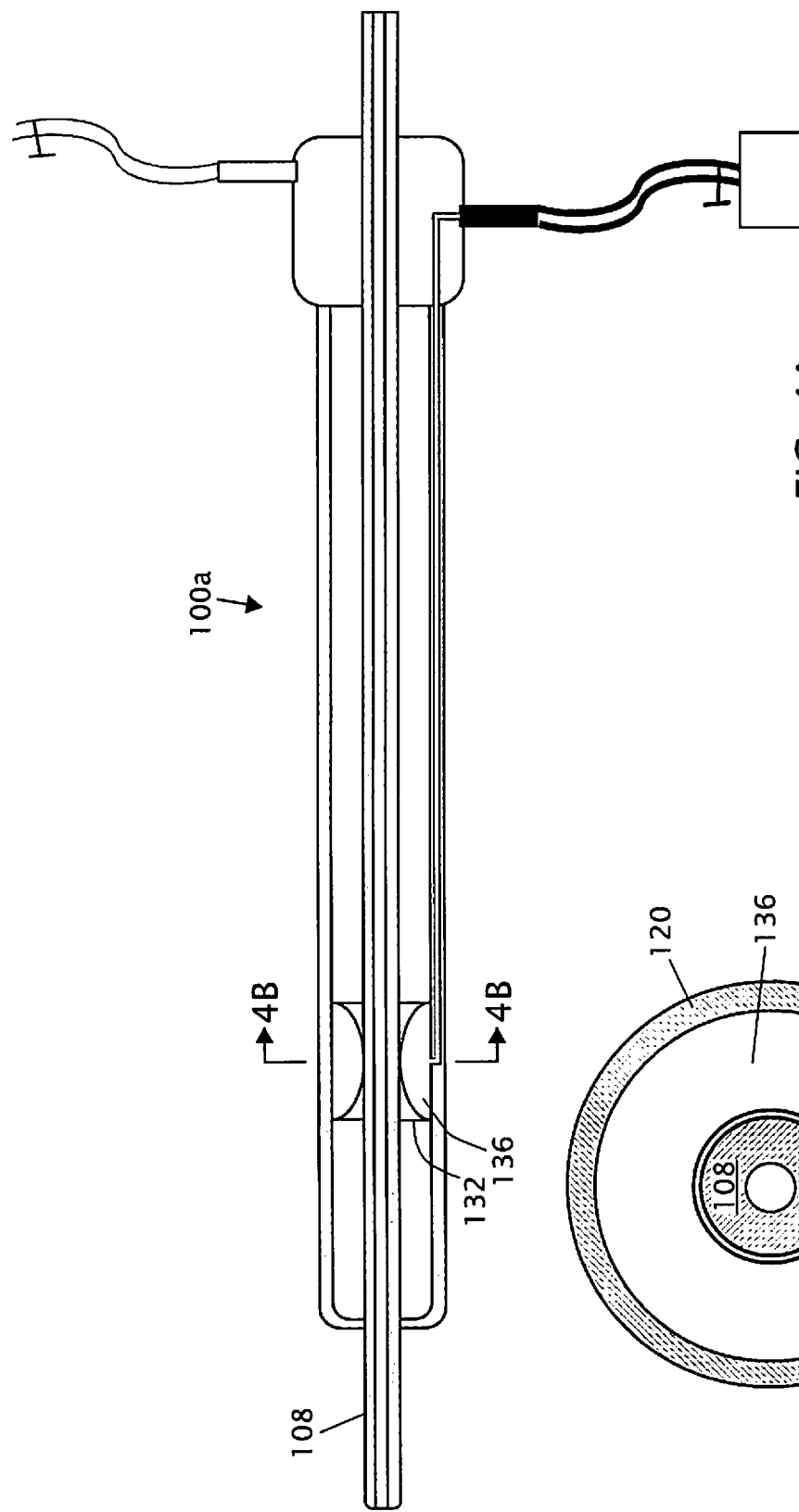
Figure 4B:
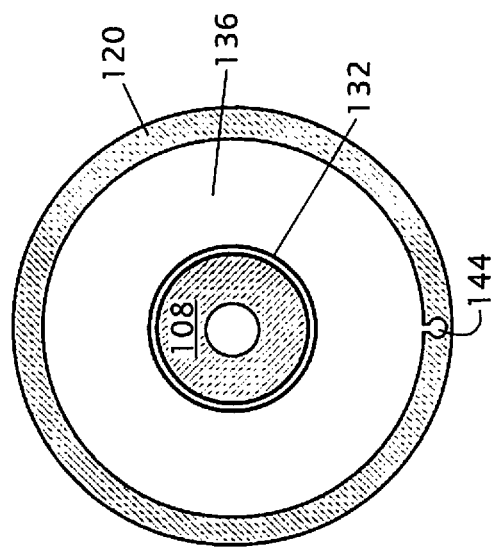

FIGS. 4A-4B depict chamber 136 inflated to expand expandable member 132 to trap a catheter 108, such as, for example, at an intermediate phase of an endovascular intervention during which expandable member 132 is trapping or stabilizing the catheter (or other device). For example, when apparatus 100a is implemented as a guide catheter (e.g., 100a-2), expandable member 132 can trap or stabilize a portion of catheter 108 (e.g., a balloon catheter) that is near the distal end of catheter 108 (e.g., during removal and/or replacement of a guidewire). Similarly, when apparatus 100a is implemented as an introducer sheath (e.g., 100a-1), expandable member 132 can trap or stabilize a portion of catheter 108 that is closer to the percutaneous insertion site (e.g., during removal and/or replacement of a guidewire).

FIG. 5 depicts a cross-sectional view of a second embodiment 100b of the present introducer sheath and catheter apparatuses. Apparatus 100b is similar to apparatus 100a, with the exception that expandable member 132a of apparatus 100b has a width 184a that is more than two times the diameter (18) of the primary lumen. In other embodiments, width 184a can be equal to any one of, or between any two of: 200%, 250%, 300%, 350%, 400%, or more of diameter 186. As indicated by line 4B-4B, for the depicted embodiment of apparatus 100b, the cross-section taken at line 4B-4B is identical to the one depicted in FIG. 4B. In such embodiments, the relatively large size of width 184a (relative to diameter 186 or other transverse dimension) can improve the stability of catheter 108 (or other device disposed in primary lumen 124), especially, for example, during procedures during which axial forces are applied to catheter 108. For example, during some instances of use (and in some embodiments of the present methods), catheter 108 can be configured to physically penetrate and/or break up a clot or other blockage in a patient's blood vessel. In such instances, axial forces may be applied to catheter 108 that may be sufficient to cause catheter 108 to deflect laterally. In such embodiments, chamber 136a can be inflated to expand expandable member 132a to stabilize and reduce lateral deflection of catheter 108. The relatively large size of width 184a (relative to diameter 186 or other transverse dimension) can improve stability by applying the stabilizing force over a larger longitudinal portion of catheter 108, thereby reducing the likelihood that the lateral deflection will simply be transferred to a different longitudinal portion of catheter 108.

Figures 6A, 6B, 6C:
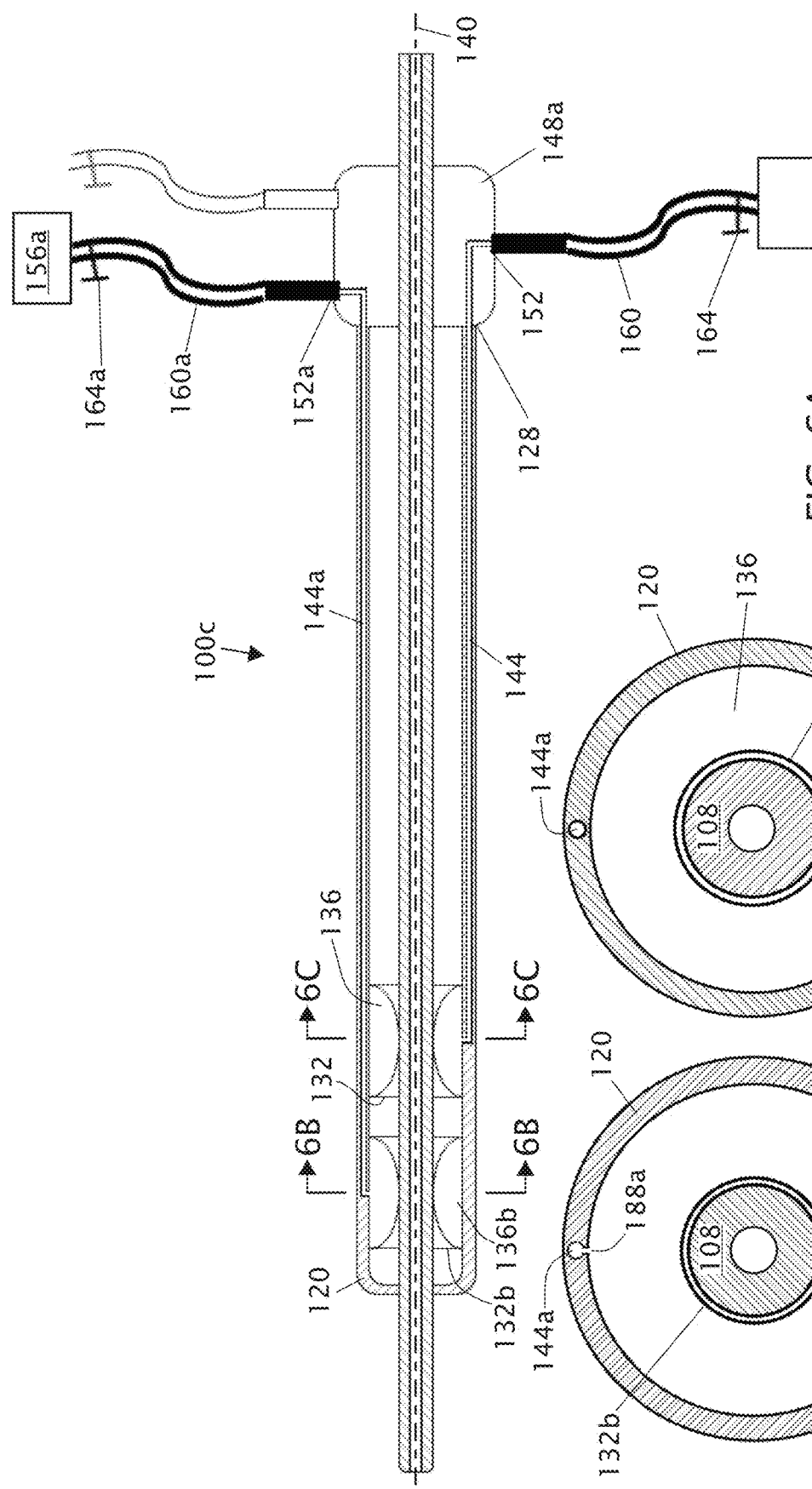
FIGS. 6A-6C depict cross-sectional views of a third embodiment of the present introducer sheaths and catheters.

FIGS. 6A-6C depict cross-sectional views of a third embodiment 100c of the present introducer sheath and catheter apparatuses. Apparatus 100c is similar to apparatus 100a, with the exception that apparatus 100c includes a second expandable member 132b longitudinally spaced along axis 140 from first expandable member 132. In some embodiments, a single secondary lumen 144 can be coupled to both chambers 136, 136b to inflate and deflate both chambers simultaneously. However, in the embodiment shown, apparatus 100c further includes a second secondary lumen 144a in fluid communication with second chamber 136b and configured to deliver fluid to expand the second expandable member (132b). In this embodiment, second secondary lumen 144a extends through sidewall 120 from proximal end 128 to chamber 136b to permit inflation and deflation of chamber 136b (through opening 188a) and the resulting expansion and contraction of expandable member 132b. In the embodiment shown, base 148a also has a second port 152a that is in fluid communication with second secondary lumen 144b and that is configured to be coupled to a fluid source (e.g., having a reservoir 156a) via a conduit 160a and valve 164a. This and others of the present multi-trapper embodiments can be especially useful for stabilizing and/or limiting lateral deflection of catheter 108 during procedures in which forces are applied axially to catheter 108, such as those described above for physically penetrating and/or breaking up a clot or other blockage in a patient's blood vessel.

FIGS. 7A-7C depict cross-sectional views of a fourth embodiment 100d of the present introducer sheath and catheter apparatuses. Apparatus 100d is similar to apparatus 100a, with the exception that apparatus 100d includes an expandable member 132c that defines chamber 136c without sidewall 120 (e.g., expandable member 132c can alone define the chamber, as in the depicted embodiment). For example, in the embodiment shown, expandable member 132c includes a donut-shaped balloon that is coupled (e.g., by adhesive, plastic weld, and/or the like) to sidewall 120 along the perimeter of primary lumen 124.

FIGS. 8A-8C depict cross-sectional views of a fifth embodiment 100e of the present introducer sheath and catheter apparatuses. Apparatus 100e is similar to apparatus 100e, with the exception that apparatus 100e includes first and second expandable members 132d, 132e that do not extend entirely around axis 140 (are not annular). In this embodiment, expandable members 132d, 132e are disposed on opposing sides of primary lumen 124 (and axis 140) from each other. Expandable members 132d, 132e are similar to expandable member 132c in that expandable members 132d, 132e defines respective chambers 136d, 136e without sidewall 120 (e.g., expandable members 132d, 132e each can alone define the respective chamber, as in the depicted embodiment). However, expandable members 132d, 132e can each be configured to have a non-circular cross-sectional shape. For example, in the embodiment shown, each of expandable members has a base portion 192 configured to be coupled (e.g., by adhesive, plastic weld, and/or the like) to sidewall 120, and a distal portion 196 that is closer to axis 140 than base portion 192. In this embodiment, base portion 192 has a length that is larger than a (e.g., by adhesive, plastic weld, and/or the like) to sidewall 120 length of the distal portion to enable each expandable member 132d, 132e to curve or arc around the sides of a device such as catheter 108, as shown, to encourage the device or catheter toward the center of primary lumen 124. In some embodiments, expandable members 132d, 132e each comprises a single sheet of material, and base portion 192 is creased relative to distal portion 196 to define the respective portions and encourage the curvature shown. In other embodiments, base portion 192 and distal portion 196 comprise two distinct sheets of material that are joined at the boundaries between base portion 192 and 196 to encourage the curvature shown.

In this embodiment, apparatus 100e further includes a second secondary lumen 144c in fluid communication with second chamber 136e and configured to deliver fluid to expand the second expandable member (132e). In this embodiment, second secondary lumen 144c extends through sidewall 120 from proximal end 128 to chamber 136e to permit inflation and deflation of chamber 136e (through opening 188b) and the resulting expansion and contraction of expandable member 132e. In the embodiment shown, base 148a also has a second port 152a that is in fluid communication with second secondary lumen 144c and that is configured to be coupled to a fluid source (e.g., having a reservoir 156a) via a conduit 160a and valve 164a. In the embodiment shown, expandable members 132d, 132e are disposed at substantially equal distances from distal end 116 and/or directly across primary lumen 124 from each other (at 180-degree intervals around the circular cross-section of primary lumen 124, as shown in FIG. 8B).

Figure 9:
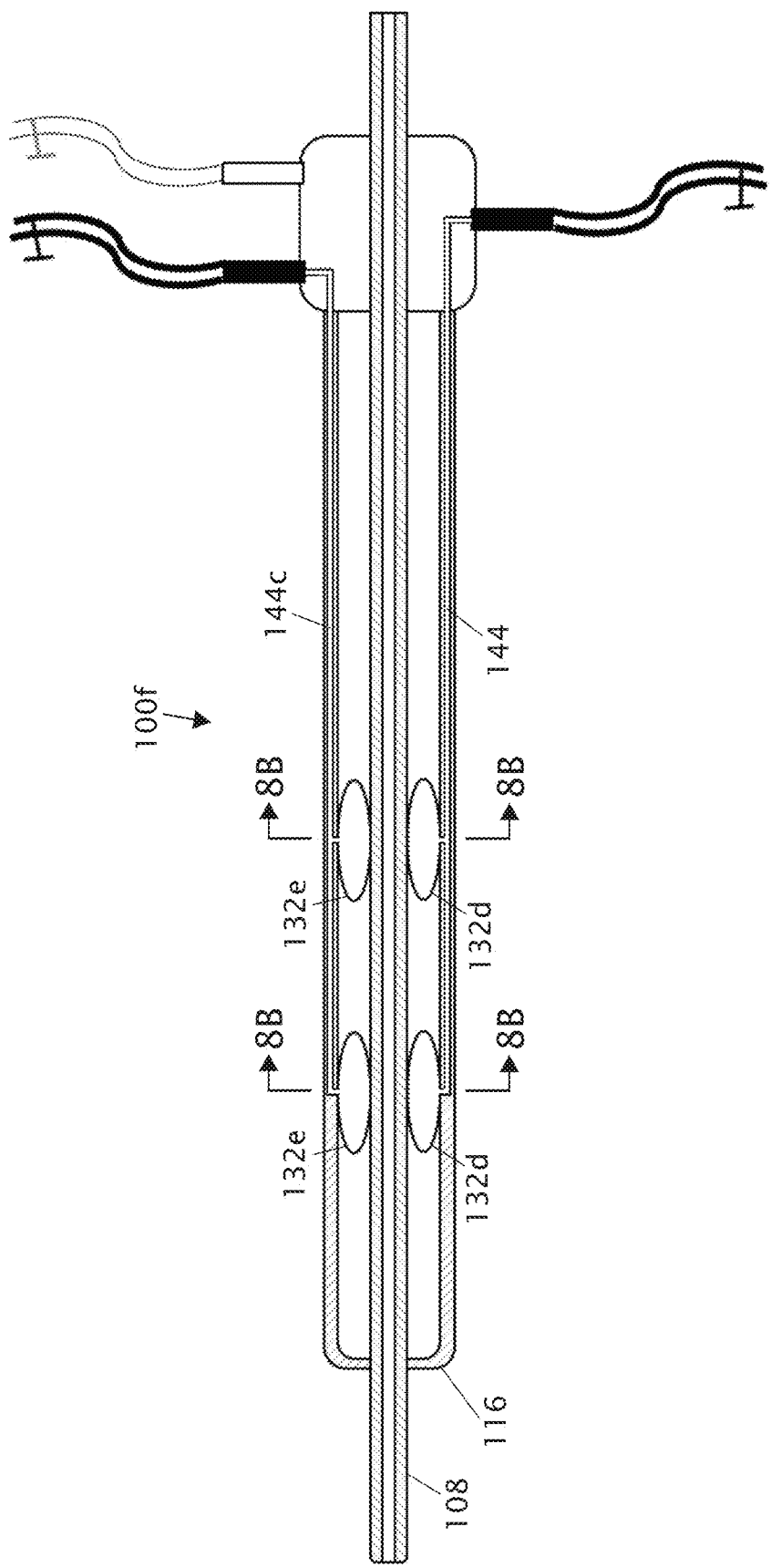
FIG. 9 depicts a side cross-sectional view of a sixth embodiment of the present introducer sheaths and catheters.

FIG. 9 depicts a cross-sectional view of a sixth embodiment 100f of the present introducer sheath and catheter apparatuses. Apparatus 100f is similar to apparatus 100e, with the exception that apparatus 100f includes a second pair of expandable members 132d, 132e, as shown. In this embodiment, both expandable members 132d are in fluid communication with first secondary lumen 144, and both expandable members 132e are in fluid communication with second secondary lumen 144c. As indicated by lines 8B-8B, for the depicted embodiment of apparatus 100f, the cross-section taken at lines 8B-8B is identical to the one depicted in FIG. 8B. This and others of the present multi-trapper embodiments can be especially useful for stabilizing and/or limiting lateral deflection of catheter 108 during procedures in which forces are applied axially to catheter 108, such as those described above for physically penetrating and/or breaking up a clot or other blockage in a patient's blood vessel.

FIGS. 10A-10D depicts cross-sectional views of a seventh embodiment 100g of the present introducer sheath and catheter apparatuses. Apparatus 100g is similar to apparatus 100f, with the exception that apparatus 100g includes a single expandable member 132d on a first side of primary lumen 124, and a pair of expandable members 132e on the opposite side of primary lumen 124. In this embodiment, the expandable members are staggered along longitudinal axis 140 (e.g., the first expandable member (132e) is closer to distal end 116 than the second expandable member (132d), and the second expandable member (132d) is closer to distal end 116 than the third expandable member (132e). In the depicted embodiment, and as shown in FIGS. 10B and 10D, expandable members 132e are radially aligned In this embodiment, expandable member 132d is in fluid communication with first secondary lumen 144, and both expandable members 132e are in fluid communication with second secondary lumen 144c. This and others of the present multi-trapper embodiments can be especially useful for stabilizing and/or limiting lateral deflection of catheter 108 during procedures in which forces are applied axially to catheter 108, such as those described above for physically penetrating and/or breaking up a clot or other blockage in a patient's blood vessel.

Figure 11A:
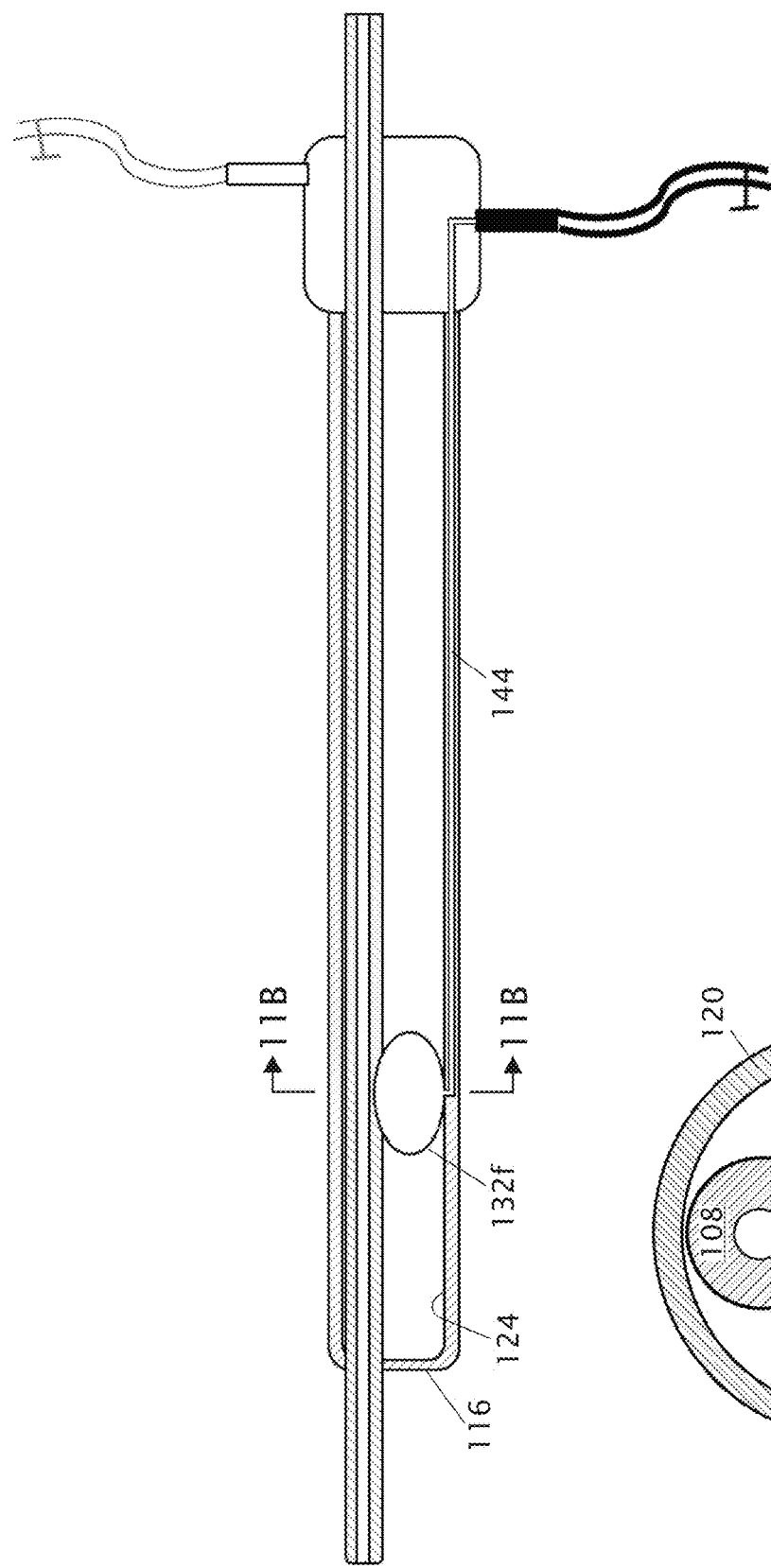
FIGS. 11A and 11B depict cross-sectional views of an eighth embodiment of the present introducer sheaths and catheters.
Figure 11B:
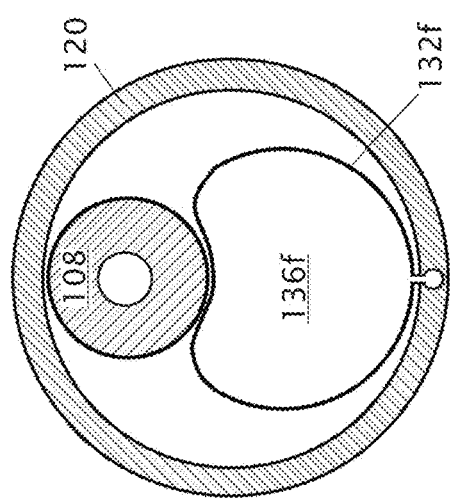

FIGS. 11A-11B depict cross-sectional views of an eighth embodiment 100h of the present introducer sheath and catheter apparatuses. Apparatus 100h is similar to apparatus 100d (FIGS. 7A-7B), with the exception that apparatus 100h includes an expandable member 132f that is not annular. Instead, in the embodiment shown, expandable member 132 is configured to have a substantially circular cross-section in the absence of a deforming force, such as may be provided by catheter 108, as shown. Notably, expandable member 132f is not shown in cross-section in FIG. 11A to show the deformation of expandable member 132f, which can permit portions of expandable member 132f to extend around the cross-sectional perimeter of catheter 108 to resist lateral motion of catheter 108 within the primary lumen (124).

Embodiments of the present apparatuses may be implemented as a variety of types of sheaths and catheters. For example, in addition to guide catheters, the present apparatuses may be implemented as other types of catheters or catheters with other types of functionality. For example, the present "grabbers" can be implemented to grasp or "tweeze" items (e.g., tools) within a vessel of a patient, such as, for example, to retrieve such items.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:
 an elongated sheath or catheter body having an outer diameter between 6 French (2 millimeters) and 9

French (3 millimeters), a proximal end, and a distal end configured for percutaneous insertion into a vessel of a patient, the elongated sheath or catheter body having a sidewall defining a primary lumen through which an elongated endovascular device can be inserted into the patient's vessel;

an expandable member coupled to the sidewall such that a chamber is configured to be inflated to expand the expandable member in a direction away from the sidewall into the primary lumen, the expandable member disposed closer to the distal end of the elongated sheath or catheter body than to the proximal end such that the apparatus is configured to position the expandable member within the vessel of the patient when the distal end of the elongated sheath or catheter body is disposed within the vessel;

a secondary lumen defined within the sidewall and a port in fluid communication with the secondary lumen, wherein the port is disposed closer to the proximal end of the elongated sheath or catheter body than to the distal end such that the apparatus is configured to position the port external to the patient when the distal end of the elongated sheath or catheter body is disposed within the vessel, the secondary lumen being elongated and having a longitudinal axis that, when the sheath or catheter body is straight, extends substantially parallel to a central longitudinal axis of the primary lumen, the secondary lumen in fluid communication with the chamber and configured to deliver fluid received through the port to expand the expandable member; and where the chamber is annular and extends entirely around the central longitudinal axis of the primary lumen, and where the expandable member defines the chamber without the sidewall.

2. The apparatus of claim 1, where the sidewall is inelastic.

3. The apparatus of claim 1, where the expandable member is a first expandable member, the chamber is a first chamber, and the apparatus further comprises:
a second expandable member coupled to the sidewall such that a second chamber is configured to be inflated to expand the second expandable member in a direction away from the sidewall into the primary lumen.

4. The apparatus of claim 3, where the second expandable member is spaced apart from the first expandable member along the central longitudinal axis of the primary lumen.

5. The apparatus of claim 3, where the secondary lumen is a first secondary lumen, and the apparatus further comprises:
a second secondary lumen in fluid communication with the second chamber and configured to deliver fluid to expand the second expandable member.

6. The apparatus of claim 1, where the expandable member has a base portion and a distal portion that is closer to the central longitudinal axis than the base portion, and the base portion has a length that is larger than a length of the distal portion.

7. The apparatus of claim 6, where the expandable member is a first expandable member, the chamber is a first chamber, and the apparatus further comprises:
a second expandable member coupled to the sidewall such that a second chamber is configured to be inflated to expand the second expandable member in a direction away from the sidewall into the primary lumen.

8. The apparatus of claim 7, where the first expandable member and the second expandable member are disposed at substantially equal distances from the distal end.

9. The apparatus of claim 8, where the secondary lumen is a first secondary lumen, and the apparatus further comprises:
a second secondary lumen in fluid communication with the second chamber and configured to deliver fluid to expand the second expandable member.

10. The apparatus of claim 7, further comprising:
a third expandable member coupled to the sidewall such that a third chamber is configured to be inflated to expand the third expandable member in a direction away from the sidewall into the primary lumen.

11. The apparatus of claim 10, where the secondary lumen is in fluid communication with the third chamber and configured to deliver fluid to expand the third expandable member.

12. The apparatus of claim 10, where the first expandable member is closer to the distal end than the second expandable member, and the second expandable member is closer to the distal end than the third expandable member.

13. The apparatus of claim 10, further comprising:
a fourth expandable member coupled to the sidewall such that a fourth chamber is configured to be inflated to expand the fourth expandable member in a direction away from the sidewall into the primary lumen;
where the first expandable member is radially aligned with the third expandable member, the second expandable member is radially aligned with the fourth expandable member, and the first expandable member is disposed opposite the primary lumen from the third expandable member.

14. The apparatus of claim 1, further comprising:
a fluid source comprising a reservoir configured to be coupled to the secondary lumen.

15. The apparatus of claim 1, wherein the width of the expandable member is more than two times a diameter of the primary lumen.

16. The apparatus of claim 1, comprising a syringe, wherein the port is configured to be coupled to the syringe.

17. A method comprising:
inserting the distal end of the body of an apparatus of claim 1 through skin of a patient and into a vessel of the patient;
disposing an elongated surgical device in the primary lumen of the apparatus; and
delivering fluid to the chamber to expand the expandable member and stabilize the elongated surgical device.

18. The method of claim 17, where the elongated surgical device stabilized by the expandable member is a guidewire, and the method further comprises:
removing a second elongated medical device from the guidewire while the guidewire is stabilized by the expandable member.

* * * * *